(12) United States Patent
Zhao

(10) Patent No.: US 10,605,946 B2
(45) Date of Patent: Mar. 31, 2020

(54) METAL DETECTION APPARATUS

(71) Applicant: Mettler-Toledo Safeline Ltd., Salford, Manchester (GB)

(72) Inventor: Yifei Zhao, Salford (GB)

(73) Assignee: Mettler-Toledo Safeline Ltd., Salford, Manchester (GB)

( * ) Notice: Subject to any disclaimer, the term of this patent is extended or adjusted under 35 U.S.C. 154(b) by 430 days.

(21) Appl. No.: 15/590,516

(22) Filed: May 9, 2017

(65) Prior Publication Data

US 2017/0371061 A1 Dec. 28, 2017

(30) Foreign Application Priority Data

Jun. 22, 2016 (EP) .................................... 16175614

(51) Int. Cl.
| | | |
|---|---|---|
| G01V 3/10 | (2006.01) | |
| G01V 3/08 | (2006.01) | |
| G01R 33/12 | (2006.01) | |
| G01N 27/72 | (2006.01) | |

(52) U.S. Cl.
CPC ................ *G01V 3/105* (2013.01); *G01V 3/08* (2013.01); *G01N 27/72* (2013.01); *G01R 33/12* (2013.01)

(58) Field of Classification Search
CPC .......... G01V 3/10; G01V 3/105; G01V 3/101; G01V 3/08; G01R 33/12; G01N 27/023; G01N 27/72; G01N 33/2858
See application file for complete search history.

(56) References Cited

U.S. PATENT DOCUMENTS

| | | | |
|---|---|---|---|
| 8,841,903 B2 | 9/2014 | Lyon | |
| 2013/0049745 A1* | 2/2013 | Lyon | ...................... G01V 3/104 324/239 |
| 2016/0291098 A1* | 10/2016 | Ellison | ................... G01V 3/105 |
| 2016/0349230 A1* | 12/2016 | Kirkjan | ................ G01N 33/025 |

FOREIGN PATENT DOCUMENTS

| | | |
|---|---|---|
| DE | 4424058 C1 | 10/1995 |
| JP | 57-127868 A | 8/1982 |
| WO | 02/25318 A1 | 3/2002 |

OTHER PUBLICATIONS

Choi, K.N., Two Channel Metal Detector using Two Perpendicular Antennas, Incheon National University, 2013, 9 pages.

* cited by examiner

*Primary Examiner* — Son T Le
(74) *Attorney, Agent, or Firm* — Standley Law Group LLP; Jeffrey S. Standley; Stephen L. Grant

(57) ABSTRACT

A metal detection apparatus has a passage channel (100) through which products (P) that may contain metal contaminants (C) pass. The apparatus has at least one transmitter unit (1) that provides transmitter signals to a transmitter coil (2) that is inductively coupled to a first and a second receiver coil (31; 32). The receiver coils are balanced and connected separately or combined to an input of a receiver unit (4). The transmitter coil has at least two coil sections (211, 212; 221, 222) that are arranged inclined to one another, with each coil section generating at least a first and a second magnetic field ($M_y$; $M_z$). Each of the first and the second receiver coils has at least a first coil section (311; 321) that is engaged in the first magnetic field and at least a second coil section (312; 322) that is engaged in the second magnetic field.

15 Claims, 12 Drawing Sheets

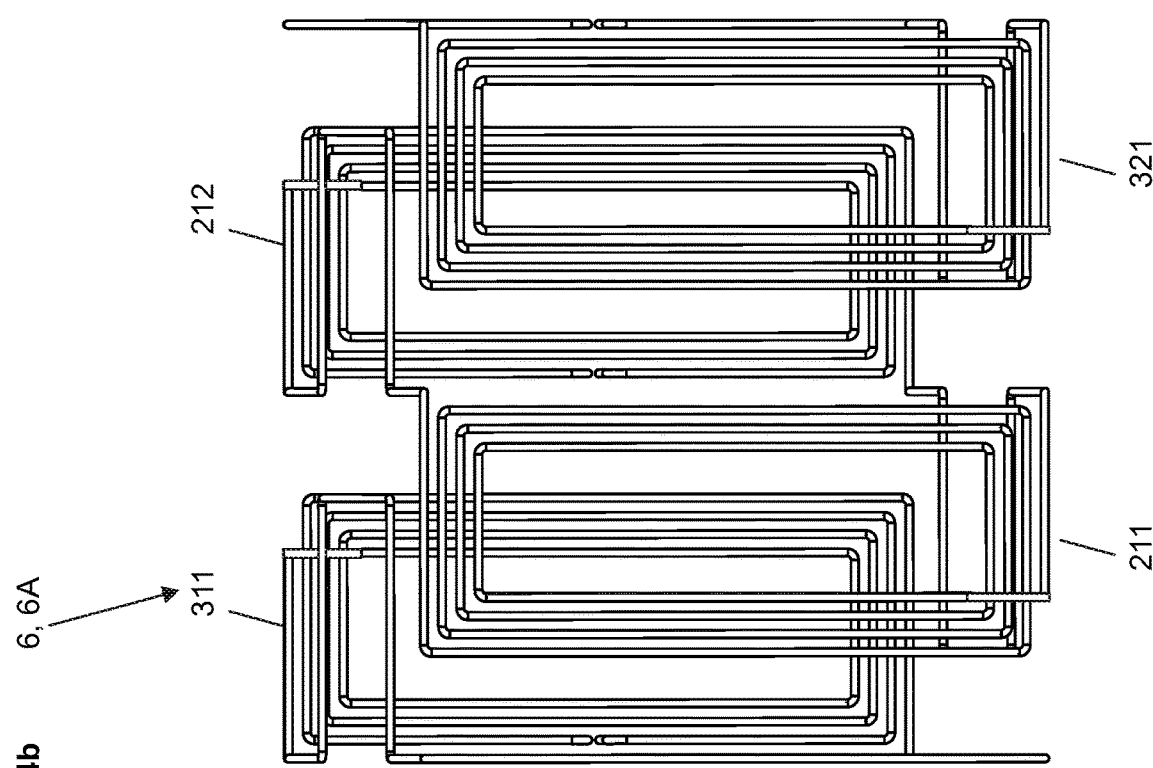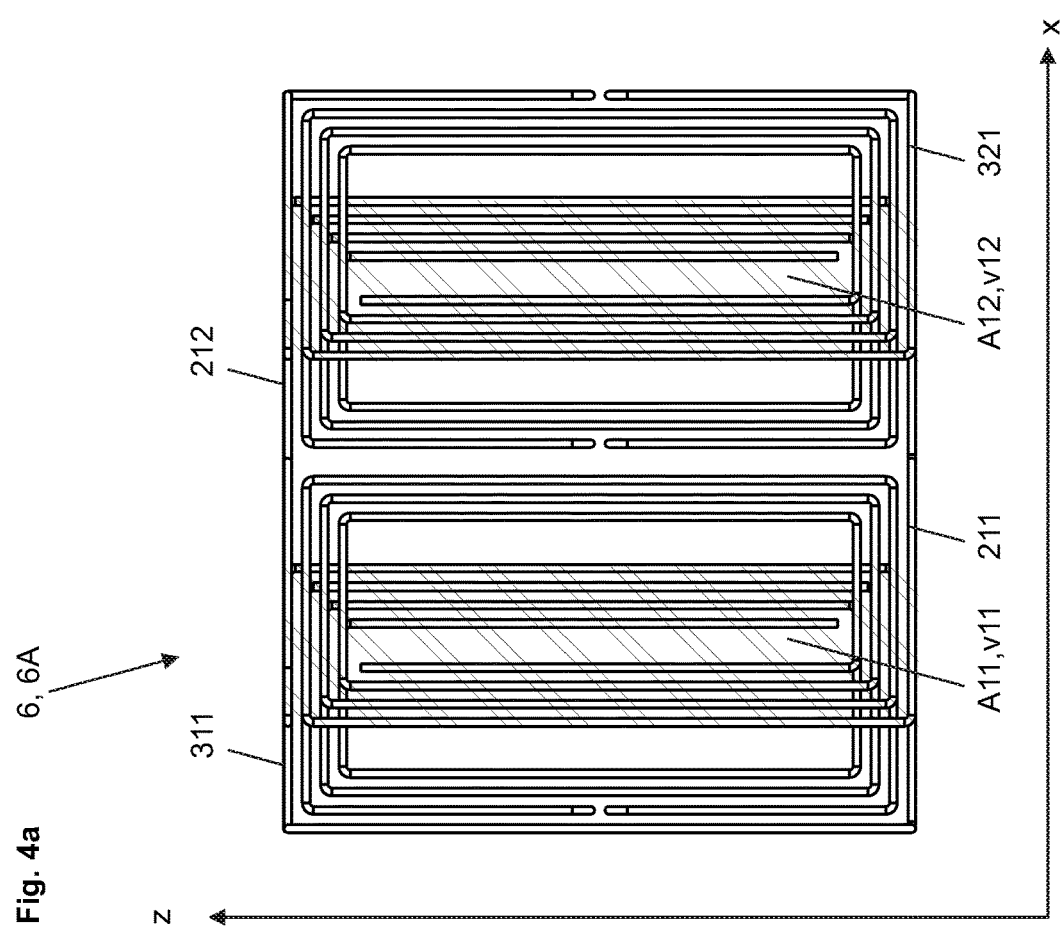

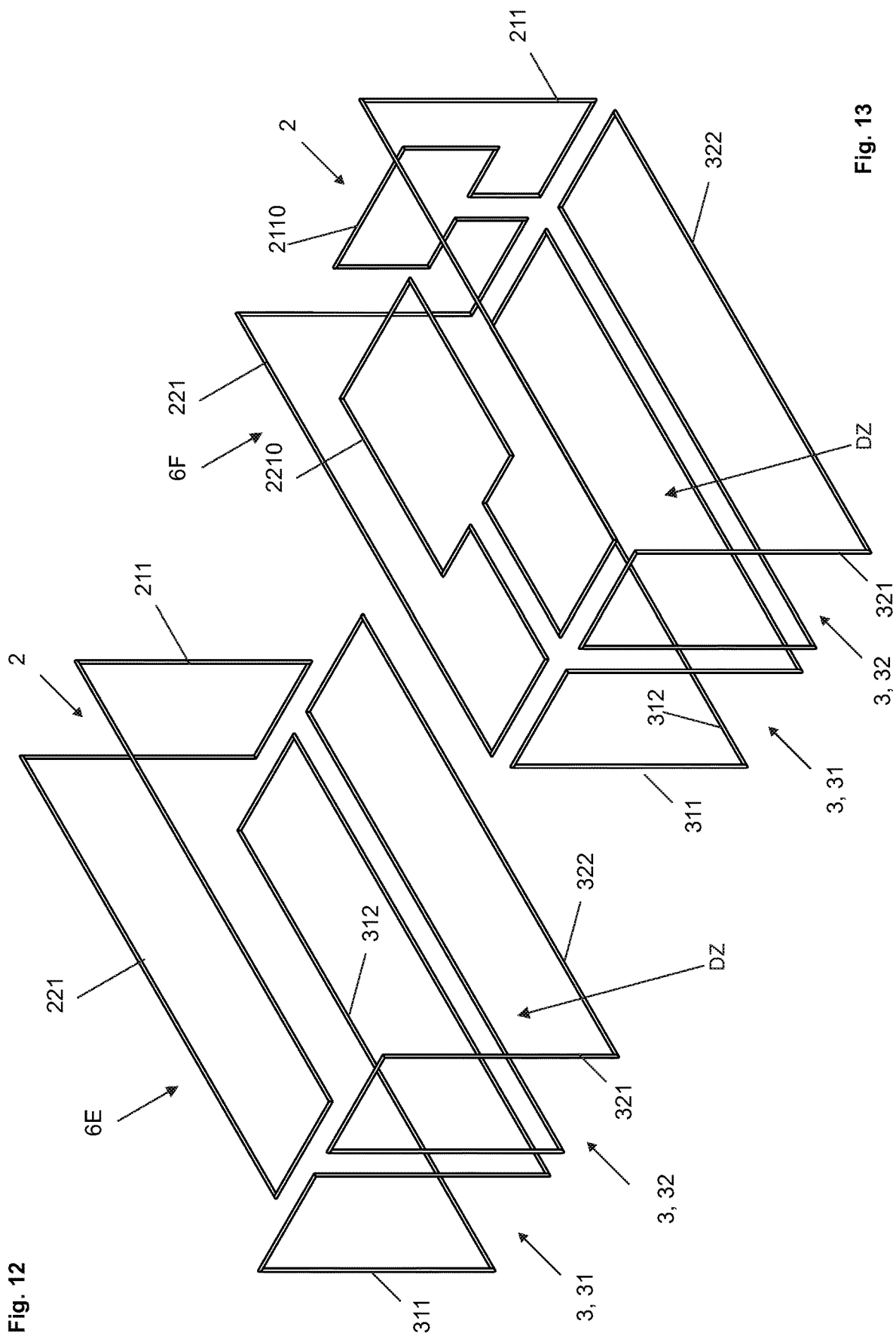

METAL DETECTION APPARATUS

CROSS-REFERENCE TO RELATED APPLICATIONS

This application claims priority under 35 USC 119 to European patent application EP 16 175 614.3, filed on 22 Jun. 2016, the content of which is incorporated by reference as if fully recited herein.

TECHNICAL FIELD

The invention relates to a metal detection apparatus that allows detection with high sensitivity of both spherical non-spherical metal particles.

BACKGROUND

A metal detection apparatus is used to detect metal contamination in edible goods and other products. As described in WO02/25318, modern metal apparatuses utilise a search head comprising a "balanced coil system" that is capable of detecting all metal contaminant types including ferrous, nonferrous and stainless steels in a large variety of products such as fresh and frozen products.

As described in U.S. Pat. No. 8,841,903 B2, a metal detection apparatus that operates according to the "balanced coil"-principle typically comprises three coils that are wound onto a non-metallic frame, each coil exactly parallel with the other. The transmitter coil located in the centre is energised with a high frequency electric current that generates a magnetic field. The two coils on each side of the transmitter coil act as receiver coils. Since the two receiver coils are identical and installed with the same distance from the transmitter coil, an identical voltage is induced in each of them. In order to receive an output signal that is zero when the system is in balance, the first receiver coil is connected in series with the second receiver coil having an inversed sense of winding. Hence the voltages induced in the receiver coils, that are of identical amplitude and inverse polarity are cancelling out one another in the event that the system, in the absence of metal contamination, is in balance.

As a metal object passes through the coil arrangement, the high frequency field is disturbed first near the first receiver coil and then near the second receiver coil. While the metal object is conveyed through the receiver coils the voltage induced in each receiver coil is changed typically in the range of nano-volts. This change in balance results in a signal at the output of the receiver coils that can be processed, amplified and subsequently be used to detect the presence of metal contamination in a product.

The signal processing channels normally split the received signal into two separate components that are 90° apart from one another. The resultant vector has a magnitude and a phase angle, which is typical for the products and the contaminants that are conveyed through the coils. In order to identify a metal object, "product effects" need to be removed or reduced. If the phase of the product is known then the corresponding signal vector can be reduced. Eliminating unwanted signals from the signal spectrum thus leads to higher sensitivity for signals originating from contaminants.

Methods applied for eliminating unwanted signals from the signal spectrum therefore exploit the fact that the contaminants, the product and other disturbances have different influences on the magnetic field so that the resulting signals differ in phase.

The signals caused by various metals or products, as they pass through the coils of the metal detection apparatus, can be split into two components, namely resistive and reactive components, according to conductivity and magnetic permeability of the measured object. The signal caused by ferrite is primarily reactive, while the signal caused by stainless steel is primarily resistive. Products, which are conductive typically cause signals with a strong resistive component.

Distinguishing between the phases of the signal components of different origin by means of a phase detector allows obtaining information about the product and the contaminants.

In known systems, the transmitter frequency is therefore selectable in such a way that the phase of the signal components of the metal contaminants will be out of phase with the product signal component.

With the arrangement disclosed in U.S. Pat. No. 8,841,903 B2, the resonant circuit, which consists of the transmitter coil and one or more tuning capacitors, can be tuned optimally and independently of other parts of the transmitter unit to the selected transmitter frequency.

This arrangement however does not address the problem that metal contamination in the product does often not provide sufficient signal response. Non-spherical metal objects will provide a signal response, which depends on the consistency of the material and its orientation to the incident magnetic field. In the metal detection system disclosed in U.S. Pat. No. 8,841,903 B2 the coils are placed in the yz-plane and the magnetic field extends along the x-axis. In unfavourable orientations, non-spherical metal may therefore not cause detectable field changes.

Because of their properties, ferrous and non-ferrous metals interact differently with the magnetic field. Ferrous metals have a magnetic permeability higher than air and therefore attract the field. When a ferrous wire is placed with a short edge leading in a metal detector, the wire is aligned in parallel to the magnetic field and causes a maximum field disturbance compared to the same wire orientated perpendicular thereto. With the first orientation of the wire magnetic flux lines are attracted and can extend over a longer distance within the wire, which therefore has a strong impact on the magnetic field. With the second orientation of the wire, magnetic flux lines only traverse the wire along a very short distance thus having a small impact on the magnetic field.

Non-ferrous metals, such as stainless steel, copper, aluminium, brass, have magnetic permeability similar to air. Therefore, the metal detector is not detecting these metals because of the change in permeability, but due to the occurrence of an alternative magnetic field caused by eddy currents that are created in the non-ferrous wire. The induced eddy currents create a magnetic field which opposes the field generated by the transmitter and reduces it locally. When a non-ferrous wire is placed with a long edge leading in a metal detector the cross-section of the wire exposed to the flow of the field is larger generating stronger eddy currents which create a stronger opposing field. In this orientation of the wire the disturbance is greater compared to orientation of this wire introduced with the short edge leading.

Consequently, depending on their consistency and orientation a metal detection apparatus may be able to detect such metal objects or not.

In order to detect metal objects with a specific orientation product could be transferred through different metal detection apparatuses which are placed one behind the other with different orientation. Such a setup of course involves considerable costs and efforts by the operator.

In an article titled "Two Channel Metal Detector using Two Perpendicular Antennas", Kyoo Nam Choi, of Incheon National University, 2013, describes a two-channel metal detection apparatus having two sets of perpendicularly oriented sensor antennas, which allow expanding the detectable size of metal particles. It is stated that a single channel metal detection sensor has not shown sensitivity resolution through a wide range of metal size. Thus, there was a need to cascade the sensors having different sensitivity resolutions.

Instead of arranging different metal detection systems, e.g. with different angle of placement, Kyoo Nam Choi proposes to use two independent sensor channels each provided with a set of antennas arranged perpendicular to one another. This arrangement requires a complex arrangement and considerable circuitry to process and evaluate the signals gained by the two antenna systems.

Japanese application JPS 57127868 A discloses a system with a plurality of rectangular excitation coils, with which magnetic fields can be applied to the product and contaminant from various directions. While the plurality of magnetic fields may enhance detectability of metal contaminations with specific form and orientation, processing the resulting signals, which will comprise various signal components with different phase and amplitude, will be difficult. Signal components of the product or contaminants may add up or cancel out possibly causing false-positive and false-negative reports of the metal detection system. Furthermore, installing and operating a plurality of excitation coils requires space and an enhanced transmitter system. Still further, mounting different excitation coils typically requires a larger volume of the coil system, thus reducing the coupling of the current system to the contaminants so that sensitivity is reduced.

It is further important to note that known metal detection apparatuses may incorporate coil systems that define detection zones having different geometrical forms. The metal detection apparatus and the geometrical form of the detection zone, which forms the passage channel for the processed products, are selected according to the application process. Often the detection zone or passage channel has a rectangular cross-section through which products are transferred by a conveyor belt. Hollow cylindrical or conical detection zones are often used in metal detection apparatuses that are used in processes, in which a product is vertically dropped into a container. Hence, the detection zones may have a cross-sectional profile that varies or is constant along the travel path of the product. Systems with conical detection zones use coils that differ in size from one another typically with the transmitter coil being off-centred between the two receiver coils. In both systems, the coils are arranged such that, when the at least one transmitter coil is energized by an alternating electric current, the electromagnetic field generated thereby induces a first voltage in the first receiver coils and a second voltage in the second receiver coil, the first and second voltages cancelling each other out when there is no metal present in the object under inspection.

The present invention is therefore based on the object of creating an improved metal detection apparatus.

In particular, the present invention is based on the object of creating an improved metal detection apparatus that allows reliable detection of metal particles independently of their consistency, geometrical form and orientation.

Particularly, the present invention is based on the object of creating a metal detection apparatus that operates with improved signal sensitivity for metal particles independently of their consistency, geometrical form and orientation.

The metal detection system shall provide improved results without requiring additional coil systems, processing channels, or additional processing efforts. Further, the metal detection apparatus shall still have a compact structure and practically equivalent dimensions compared to known metal detection apparatuses.

Furthermore, the metal detection system shall be created such that a close coupling of the coil system to contaminants contained in a processed product is reached.

Still further, the invention shall be applicable to any type of metal detection apparatus with any kind of detection zone or passage channel that may be for example rectangular, hollow cylindrical or conical.

SUMMARY

These and other objects of the present invention are achieved by a metal detection apparatus as defined in the appended claims.

The metal detection apparatus, which has a passage channel for transferring products that may contain metal contaminants, comprises at least one transmitter unit, which provides transmitter signals to a transmitter coil that is inductively coupled to a first and a second receiver coil, which are balanced and connected separately or combined to an input of a receiver unit.

According to the invention the transmitter coil comprises at least two coil sections that are arranged inclined to one another and that generate at least a first and a second magnetic field and wherein the first and the second receiver coil comprise each at least a first coil section that is engaged in the first magnetic field and at least a second coil section that is engaged in the second magnetic field.

Preferably the at least two coil sections of the transmitter coil as well as the magnetic fields generated therewith are preferably aligned perpendicular to one another, preferably such that at least one intersection of the two magnetic fields is generated within the passage channel. Hence, with one transmitter coil two or three electromagnetic fields can be generated that extend in different directions, which are preferably aligned perpendicular to one another.

Hence, non-spherical metal objects will always strongly influence at least one of the two or three magnetic fields, independently of its orientation and consistency so that any metal object in any orientation can be sensed by the at least one first and second section of the two balanced receiver coils with high sensitivity.

With two receiver coils, which are preferably combined to a single balanced receiver coil and the transmitter coil, a two-dimensional detection zone with two magnetic fields that preferably have at least one common intersection zone or a three-dimensional detection zone with three magnetic fields that preferably have at least one common intersection zone is created. Changes of the magnetic flux of the two or three magnetic fields generated in the detection zone can be sensed by means of the balanced receiver coils.

Hence, with the same number of coils as used in conventional metal detection apparatuses the inventive metal detection apparatus allows establishing a detection zone with two or three magnetic fields present. A significant increase in sensitivity is reached not only for non-spherical metal objects but also for spherical metal objects.

In a basic embodiment, the transmitter coil and the receiver coils may be L-shaped having two coil arms with even or different lengths, which enclose an angle of preferably 90°. With this transmitter coil two strong electromagnetic fields can be established in the detection zone. In this embodiment, the two receiver coils may be identical to the transmitter coil but are arranged inverse relative to the transmitter coil, so that the L-shaped transmitter coil and the L-shaped receiver coils embrace the passage channel. In general, the transmitter coil (see e.g. FIG. 12) may not necessarily form a closed loop in a specific plane (e.g. the xz-plane), wherefore no electromagnetic field is generated in this plane (e.g. along the x-axis).

In a further preferred embodiment, the coil sections of the transmitter coil and the coil sections of the first receiver coil and the coil sections of the second receiver coil form closed loops distant from one another in third parallel planes. The transmitter coil generates a third magnetic field with its closed loop that is sensed by the closed loops of the receiver coils. In a new perpendicular to the third parallel planes, the closed loops of the transmitter coil and receiver coils correspond to the closed loops of the conventional metal detection apparatuses.

In this preferred embodiment, the inventive transmitter coil is designed to generate magnetic fields in all three dimensions and the receiver coils are designed to sense changes of the magnetic field in all three dimensions. Inventive coil systems allow therefore generating electromagnetic fields in any two dimensions or in all three dimensions.

In preferred embodiments, the transmitter coil comprises pairs of interacting coil sections that generate one of the magnetic fields. Interacting coil sections are arranged for example on the left and right side or on top and bottom of the passage channel.

A coil section of the transmitter coil or the receiver coils is therefore primarily dedicated to generating or sensing a magnetic field that is aligned in one dimension (e.g. along the y-axis or z-axis) but may also contribute as a part of a closed loop to the generation of a magnetic field into another dimension (e.g. the x-axis). A rectangular transmission coil consists therefore of four coil sections, which may comprise different elements or elements with different shape.

The windings of each individual section of the transmitter coil can be selected as required. Preferably, the windings are selected according to the aspect ratio of the cross-section of detection zone, which at least approximately corresponds to the cross-section of the passage channel.

In a further preferred embodiment, the coil sections of the transmitter coil comprise a first and a second coil section that are arranged distant from one another in first parallel planes, which preferably correspond to sidewalls of the passage channel. With this pair of the first and second coil sections the first magnetic field is generated. The coil sections of the transmitter coil further comprise a third and a fourth coil section that are arranged distant from one another in second parallel planes, which preferably correspond to the bottom and top side of the passage channel. With this pair of third and fourth coil sections the second magnetic field is generated. The distance between the two first planes and the distance between the two second planes define the width and the height, i.e. the aspect ratio of the passage channel. In the event that the width and the height of the passage channel are equivalent, then the number of turns of the first and second coil sections and the number of turns of the third and fourth coil sections will be equivalent. In the event that the width is twice as large as the height of the passage channel, then the number of turns of the first and second coil sections is preferably double as high as the number of turns of the third and fourth coil sections. With pairs of interacting first and second coil sections or interacting third and fourth coil sections having a number of terms accordingly selected a magnetic field can be defined with high homogeneity across a large area.

In preferred embodiments, the balanced first and second receiver coils are arranged point-symmetrically or axis-symmetrically relative to one another. In addition, or alternatively thereto, the transmitter coil is designed point-symmetrically or axis-symmetrically and is located in the centre between the first and second receiver coils.

With this arrangement, particularly with point-symmetrically arranged or designed coils, close coupling of the coils and a compact design of the coil system can be reached.

In a further preferred embodiment the first coil sections of the receiver coils are arranged distant from one another within or in parallel to the first planes, in which the first or the second coil sections of the transmitter coil are present, and the second coil sections of the receiver coils are arranged distant from one another within or in parallel to the second planes, in which the third or fourth coil sections of the transmitter coil are present.

The coil sections of the transmitter coil and the receiver coils are therefore arranged in common planes, so that's no additional space is required in comparison with conventional metal detection apparatuses.

The first, second and third magnetic fields, if present, are aligned at least approximately orthogonal to one another.

In preferred embodiments, the coil sections of the transmitter coil or the coil sections of the transmitter coil and the coil sections of the receiver coils delimit a detection zone on four sides. The detection zone has preferably a rectangular profile, a cylindrical profile or a conical profile that corresponds at least approximately to the passage channel. In the event that the passage channel has a rectangular profile, then the aspect ratio is selected preferably in the range from 1:1 to 1:10.

The design of the coil system can easily be adapted from a rectangular profile to a hollow cylindrical profile by bending the transmitter coil and receiver coils accordingly. In the event that a conical profile is selected, then the dimensions of the coils particularly of the receiver coils and their distances to the transmitter coil are adapted accordingly so that the system remains in balance.

The first and second coil sections of the transmitter coil and the first coil sections of the receiver coils, which are arranged distant from one another in the first parallel planes, preferably overlap one another in a projection perpendicular to the first planes thus defining at least a first area of overlap.

The third and fourth coil sections of the transmitter coil and the second coil sections of the receiver coils, which are arranged distant from one another in the second parallel planes, preferably overlap one another in a projection perpendicular to the second planes thus defining at least a second area of overlap.

The closed loops formed by the transmitter coil, the first receiver coil and the second receiver coil, which are arranged distant from one another in the third parallel planes, overlap one another in a projection perpendicular to the third planes thus defining at least a third area of overlap.

The areas of overlap form cross sections of primary volumes that extend perpendicular or inclined to the related area of overlap and form at least one intersection defining a secondary volume in which the first and/or the second and/or the third magnetic fields at least partially intersect. A metal object travelling through this secondary volume will impair or modulate all magnetic fields present in this secondary volume more or less depending on its orientation and consistency. The at least one secondary volume is therefore the preferred space for passing products for inspection.

The coil sections of the transmitter coil, which are magnetically interacting with one another, are preferably provided with an identical shape that may be symmetrical or asymmetrical. As well, the coil sections of the transmitter coil and coil sections of the receiver coils, which are magnetically interacting with one another are preferably provided with a shape identical to the corresponding coil sections of the transmitter coil.

The first coil sections of the receiver coils preferably have the same shape as the related first or second coil section of the transmitter coil and extend into the same or preferably opposite direction. The second coil sections of the receiver coils preferably have the same shape as the related third or fourth coil section of the transmitter coil and are extending in the same or preferably opposite direction.

The coil sections of the transmitter coil and/or the coil sections of the receiver coils or elements thereof may have for example a rectangular, circular, curved, sinusoidal, trapezoidal, or saw-tooth-shape.

The transmitter coil and the receiver coils are wound preferably onto a non-conductive coil form, which comprises grooves designed for receiving the transmitter coil and/or the receiver coils.

The coil form preferably consists of four panels, which are independently manufactured and assembled. The coil system can therefore be produced with little effort. The coils can be made with any suitable wire. The grooves provided in the coil form correspond to the desired number of turns. The cross sections of the grooves are selected such that each groove may receive a predetermined number of layers of the wire.

BRIEF DESCRIPTION OF THE DRAWINGS

Some of the objects and advantages of the present invention have been stated, others will appear when the following description is considered together with the accompanying drawing, in which:

FIG. 4a shows the coil system 6, 6A of FIG. 2 in a view perpendicular to the xz-plane with coil sections 211, 311 and 212, 321 of the transmitter coil 2 and the receiver coils 31, 32 overlapping in separate areas A11 and A12, respectively;

FIG. 4b shows the coil system 6, 6A of FIG. 4a from an elevated angle from which the mentioned coil sections 211, 311 and 212, 321 can be identified;

FIG. 12 shows an inventive coil system 6E in a further embodiment with an L-shaped transmitter coil 2 and two L-shaped receiver coils 31, 32; and FIG. 13 shows an inventive coil system 6F in a further embodiment with two L-shaped receiver coils 31, 32 and an L-shaped transmitter coil 2 that is provided with first and second coil sections 211, 221, that comprise each a rectangular subsection 2210, 2210.

DETAILED DESCRIPTION

Figure 1:
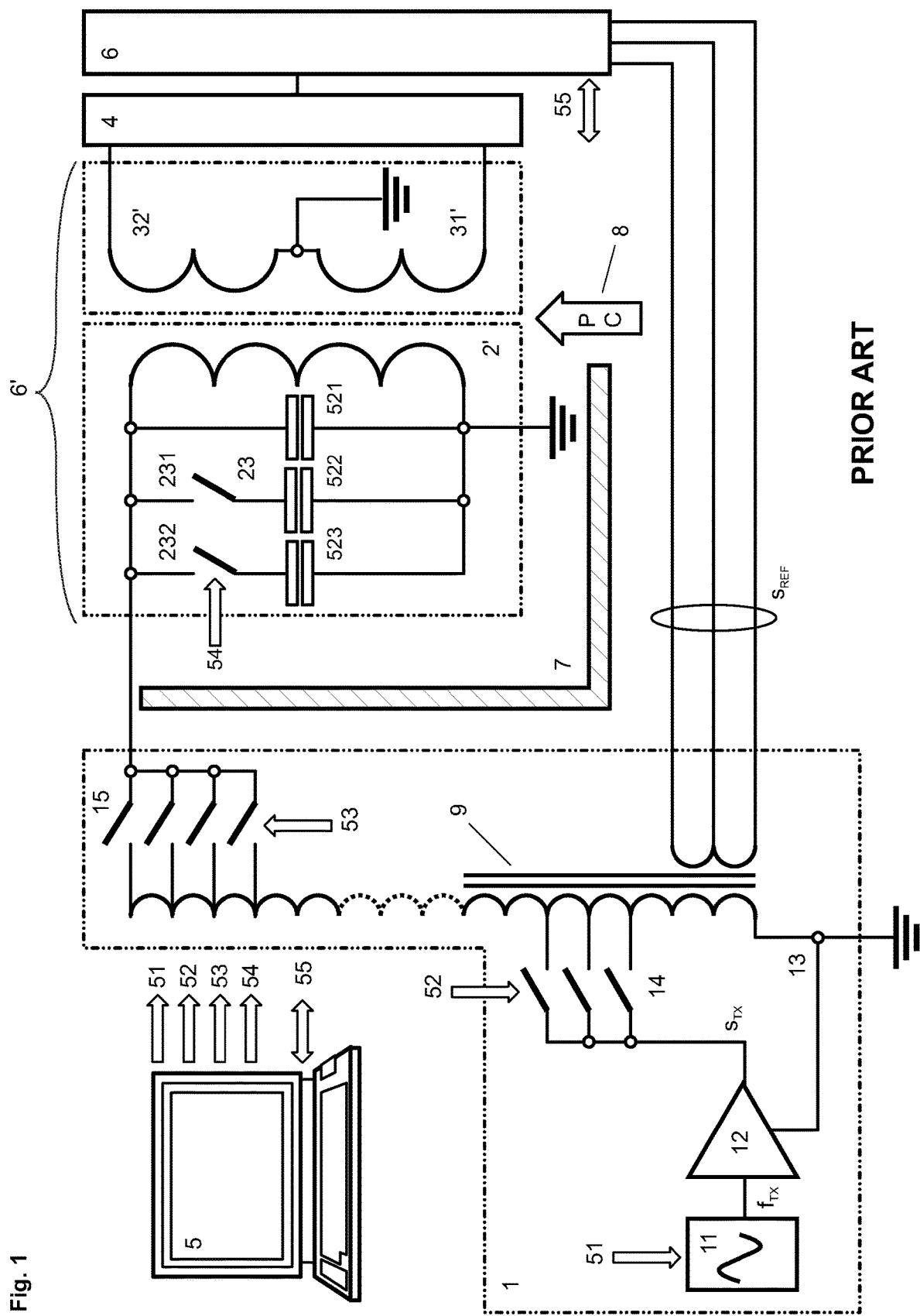
FIG. 1 shows a block diagram of the metal detection apparatus disclosed in U.S. Pat. No. 8,841,903B2.

FIG. 1 shows a block diagram of the metal detection apparatus disclosed in U.S. Pat. No. 8,841,903B2, which can be upgraded to an inventive metal detection system by installing an inventive coil system 6, 6A, 6B, 6C, 6D, 6E, 6F as shown in FIG. 2 to FIG. 12 or derivatives thereof.

The metal detection system of FIG. 1 comprises a transmitter unit 1, a balanced coil system 6' with a transmitter coil 2', a first and a second receiver coil 31', 32', a receiver unit 4, a signal processing unit 6, and a control unit 5 that comprises standard interfaces, input devices and output devices, preferably a keyboard and a monitor. FIG. 1 further symbolically shows a conveyor 8, on which products P, which may comprise metal contaminants C, are transferred through a passage channel of the metal detection apparatus i.e. through a detection zone provided by the balanced coil system 6'.

The transmitter unit 1 comprises a frequency generator 11 that provides a signal with an operating frequency $f_{Tx}$ to the input of a power amplifier 12 that operates for example according to class A or B standard. The output of the power amplifier 12 is applied preferably via a switch of a first switch bank 14 to a tap of a first group of taps of a single winding of a transformer 13, which comprises a second group of taps and which is wound around a core 9, e.g. a cylindrical ferrite core preferably of the pot-core type.

The transmitter coil 2' is connected via a switch of a second switch bank 15 to a tap of the second group of taps.

Further, a tuning capacitor 521 is firmly connected to the taps of the transmitter coil 2' thus forming a resonant L-C circuit, which is tuned to a first operating frequency $f_{TX}$ of the metal detection apparatus. Over a switch bank 23 with switches 231, 232 additional tuning capacitors 522, 523 can be connected in parallel to the first tuning capacitor 521 in order to adjust the resonant frequency of the resonant circuit to further operating frequencies $f_{Tx}$ that can be selected at the frequency generator 11.

The prior art metal detection apparatus comprises a control unit 5 that controls via control line 51 the frequency generator 11, via control line 52 the settings of the switch bank 14, via control line 53 the switch bank 15 and via control line 54 the switches 231, 232 of the tuning capacitors 522, 523 of the resonant circuit. Further, the control unit 5 is connected to the signal processing unit 6 via communication channel The control unit 5 preferably comprises a computer program that supports automated operation of the inventive metal detection apparatus.

Figure 2:
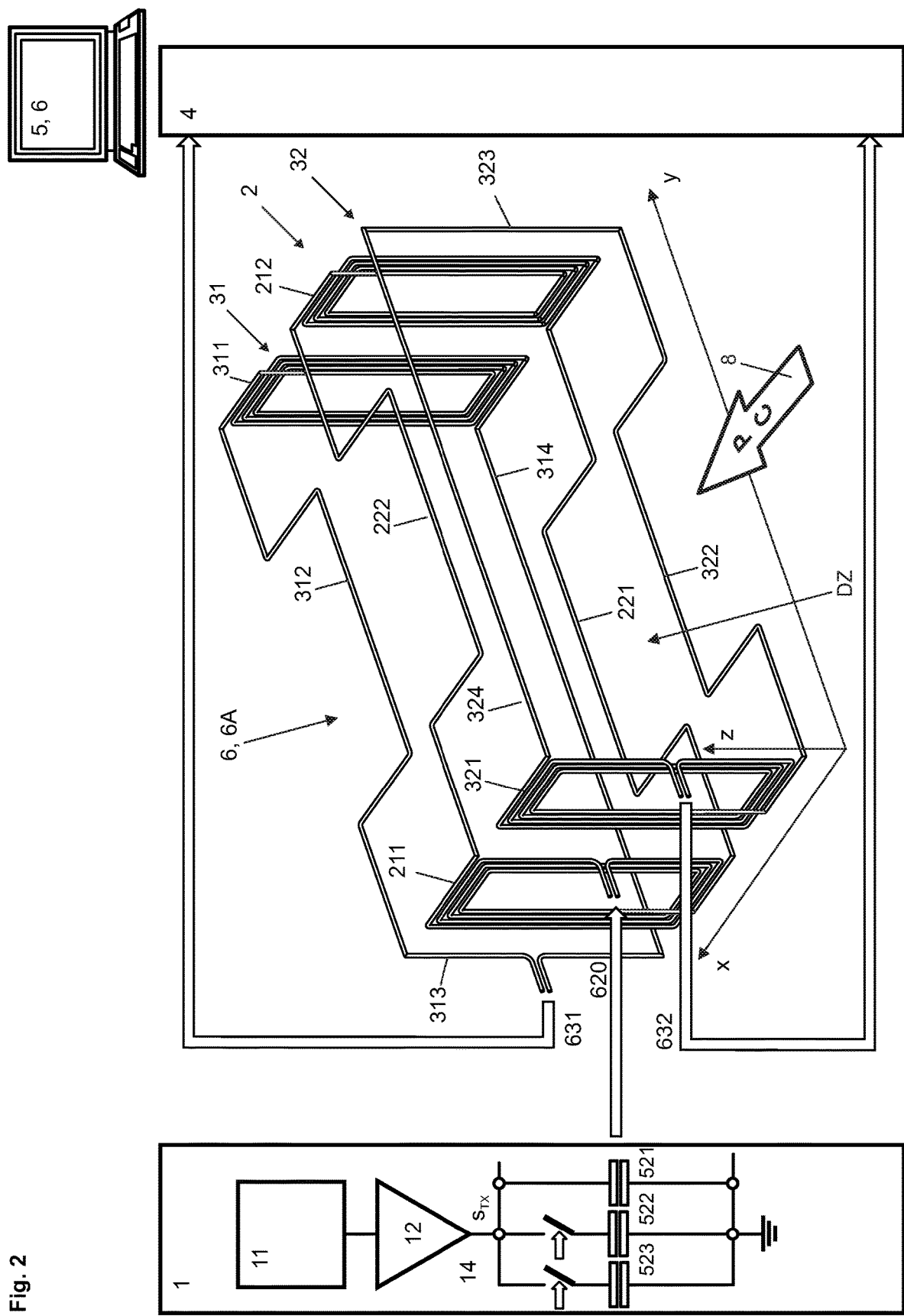
FIG. 2 shows a block diagram of an inventive metal detection apparatus which comprises a transmitter 1 and a receiver 4, for example in the embodiment of FIG. 1, and an inventive coil system 6, 6A, connected thereto, which comprises a transmitter coil 2 and two receiver coils 31, 32.

FIG. 2 shows a block diagram of an inventive metal detection apparatus which comprises a transmitter 1 and a receiver 4, for example in the embodiment of FIG. 1 and an inventive coil system 6, 6A, connected thereto, which comprises a transmitter coil 2 and two receiver coils 31, 32. Hence, the inventive coil system 6 can be installed in any known or future metal detection system. The transmitter coil 2 may be tuneable or not; i.e. the power amplifier 12 can be connected directly or via a tuning circuitry to the transmitter coil 2.

The coil system 6, which in FIG. 2 is shown in a first embodiment 6A, comprises a transmitter coil 2 arranged between the first and second receiver coil 31, 32. The coil system is embedded in a coordinate system with axes x, y, z defining planes xy, xz, and yz.

Figure 3:
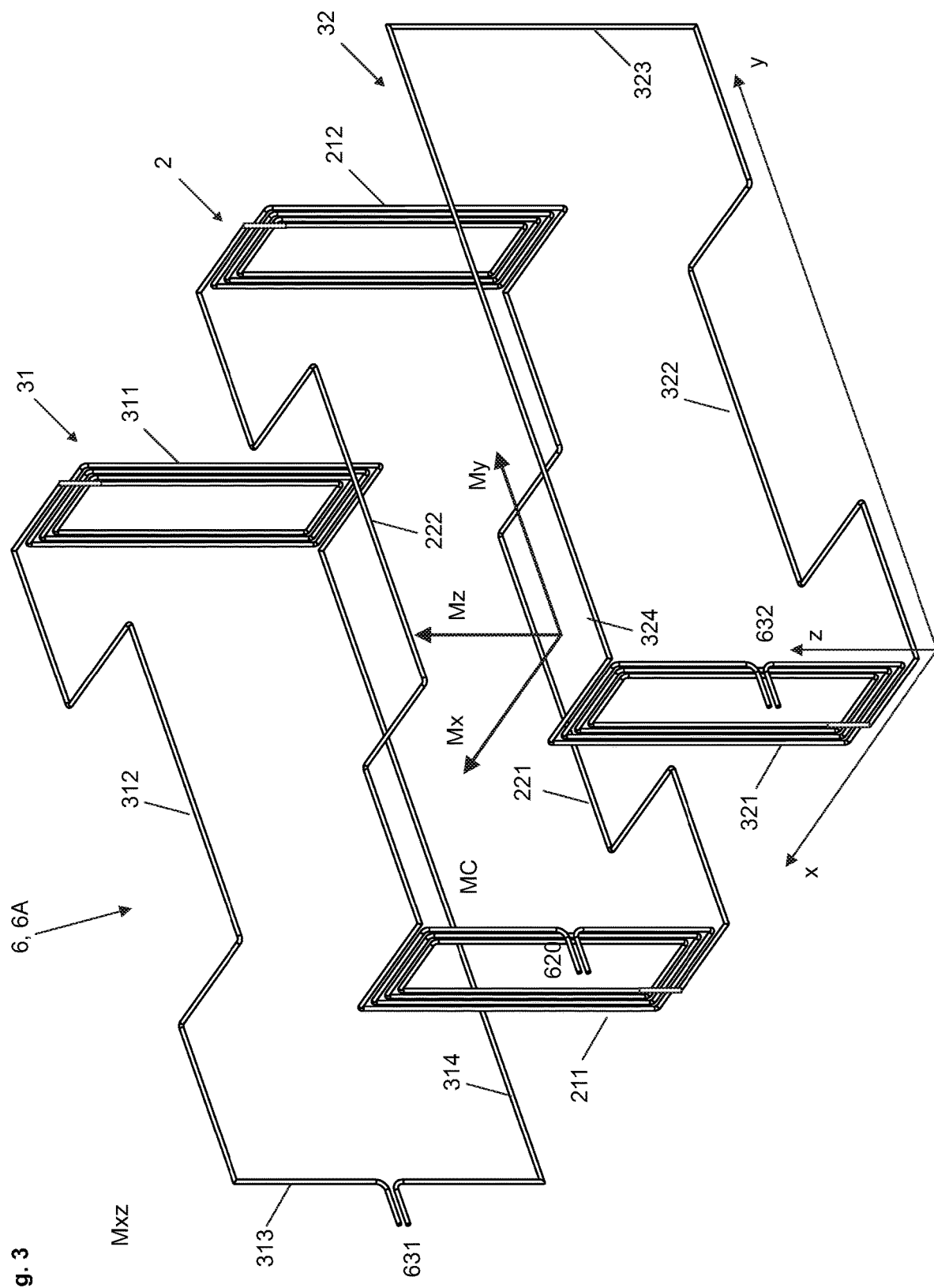
FIG. 3 shows he coil system 6, 6A of FIG. 2 in explosion view.

FIG. 3 shows the coil system 6, 6A of FIG. 2 in explosion view. The receiver coils 31, 32 have been moved in opposite directions. In specific embodiments the receiver coils are held movable relative to the transmitter coil 2 so that the coil system 6 is adjustable.

FIG. 2 and FIG. 3 show the coil system 6, 6A in spatial view. FIG. 3 symbolically shows that the transmitter coil 2 generates three magnetic fields My, Mz, Mx that are extending perpendicular to one another. The transmitter coil 2 comprises four coil sections 211, 212, 221, 222, which interact with one another in pairs 211, 212; 221, 222. The first and the second coil sections 211, 212 generate a first magnetic field My extending in parallel to the y-axis of the coordinate system. The third and fourth coil sections 221, 222 generate a second magnetic field Mz extending in parallel to the z-axis of the coordinate system. All coil sections 211, 212, 221, 222 of the transmitter coil 2 together form a closed loop that generates a third magnetic field Mx extending in parallel to the x-axis of the coordinate system.

The first and the second coil sections 211, 212 are approximately planar coils with three turns each having a rectangular shape. The third and fourth coil sections 221, 222 include a rectangular half loop each provided with a symmetrical rectangular shape in between the first and second coil sections 211, 212. All coil sections 211, 212, 221, 222 are arranged point-symmetrically. I.e., by point reflection or inversion in a point the coil sections 211, 221 are transformed into the coil sections 212, 222, and vice versa. Thereby, the interacting coil sections 211, 212 and 221, 222, respectively, are extending in opposite directions.

The receiver coils 31, 32 are arranged point-symmetrical relative to one another. I.e., by point reflection or inversion in a point the first receiver coil 31 is transformed into the second receiver coil 32, and vice versa. Thereby, the corresponding coil sections 311, 321 and 312, 322, respectively, are extending in opposite directions.

Figures 5A, 5B:
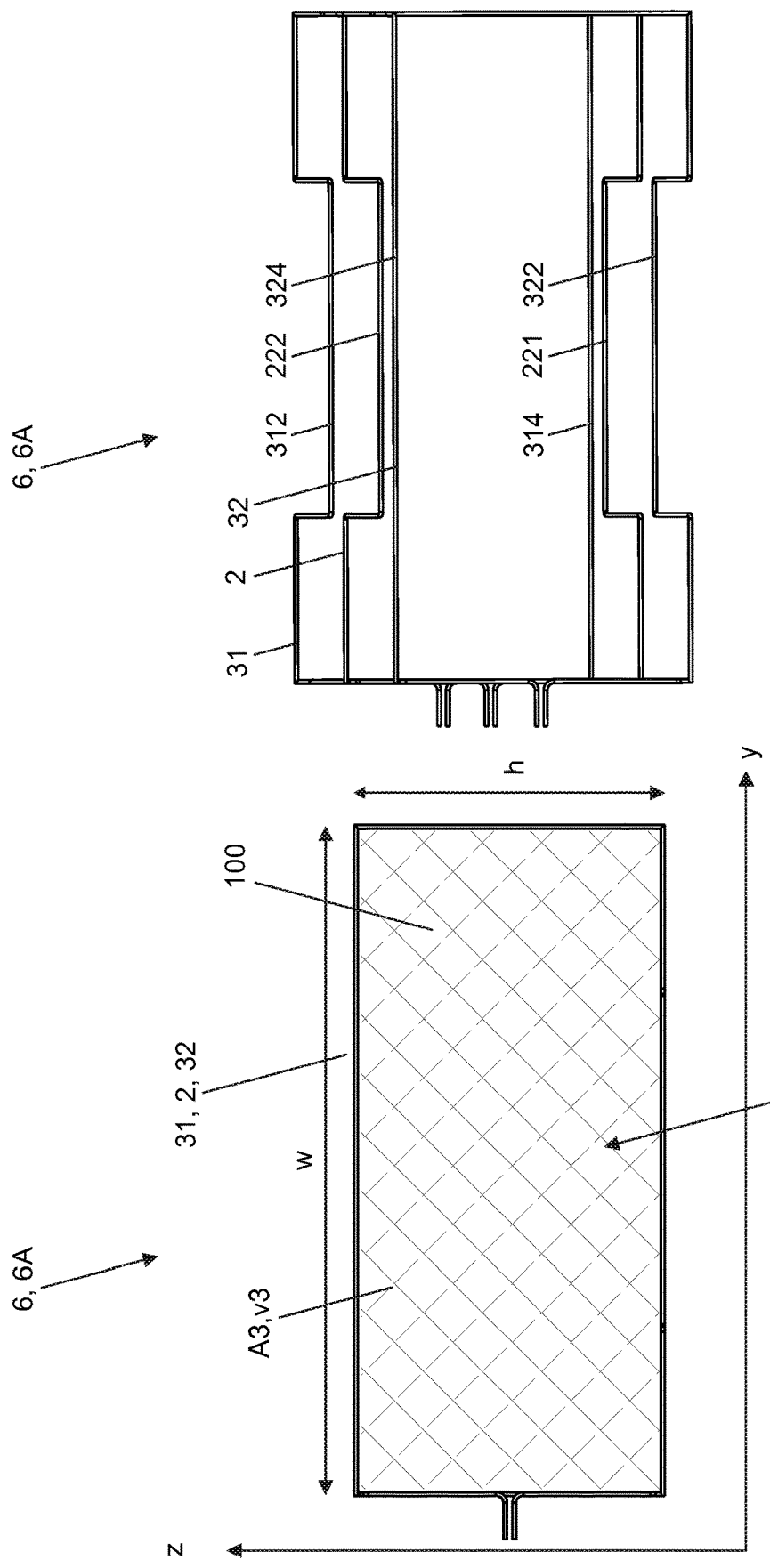
FIG. 5a shows the coil system 6, 6A of FIG. 2 in a view perpendicular to the yz-plane with the transmitter coil 2 and receiver coils 31, 32, which in this plane for closed loops, overlapping in an area A3.
FIG. 5b shows the coil system 6, 6A of FIG. 5a from an elevated angle from which the transmitter coil 2 and receiver coils 31, 32 can be identified.

All coil sections of the coil system 6, 6A are embedded within a rectangular sleeve (see FIG. 5a).

The inventive coil system 6, 6A defines therefore a detection zone DZ that is delimited on four sides by the coil sections 211, 212; 221, 222 of the transmitter coil 2, preferably by the coil sections 211, 212; 221, 222 of the transmitter coil 2 and the coil sections 311, 312, 313, 314; 321, 322, 323, 324 of the receiver coils 31, 32. The detection zone DZ, which preferably corresponds at least approximately to the passage channel 100, has preferably a hollow cylindrical profile, a conical profile or a rectangular profile whose cross-section has an aspect ratio preferably in the range from 1:1 to 1:10. Form and dimension of the passage channel and detection zone are preferably selected according to the processed products and the production process in which the metal detection apparatus is applied.

The coils 2; 31, 32 could also be arranged symmetrically relative to an axis or relative to a plane. The point-symmetrical setup shown in the drawings allows a particular compact arrangement of the coil system 6, 6A and a good coupling with the transferred material. However any of the three setups, point-symmetrical, axis-symmetrical or plane-symmetrical, will deliver significantly improved results compared to a conventional metal detection apparatus.

The coil sections 311, 312, 313, 314; 321, 322, 323, 324 of the two receiver coils 31, 32 comprise each a first coil section 311; 321 comprising three turns and being designed to sense the first magnetic field My that is extending along the y-axis. The first coil sections 311; 321 are extending in opposite directions and have the same design as the first and second coil sections 211, 212 of the transmitter coil 2 and are interacting therewith.

The second coil sections 312, 322 of the receiver coils 31, 32, with which the second magnetic field Mz is sensed, interact with the third and fourth coil section 221, 222 of the transmitter coil 2 and have the same rectangular shape and number of turns in a central part.

With the third and fourth coil sections 313, 314; 323, 324 each receiver coil 31, 32 is forming a closed loop, with which the third electromagnetic field Mx is sensed.

Due to their point-symmetric design the transmitter coil 2 and receiver coils 31, 32 can be moved closely against one another so that a compact construction of the coil system 6, 6A results and excellent coupling is achieved.

FIG. 3 shows further that the first and second coil section 211, 212 of the transmitter coil 2 and the first coil sections 311, 321 of the receiver coils 31, 32 are arranged distant from one another in first parallel planes and that the third and a fourth coil section 221, 222 of the transmitter coil 2 and the second coil sections 312, 322 of the receiver coils 31, 32 are arranged distant from one another in second parallel planes. It is further shown that the transmitter coil 2 and the receiver coils 31, 32 form closed loops, which are arranged in third parallel planes (see FIG. 5a).

This coil system 6, 6A shown in FIG. 2 and FIG. 3 provides high sensitivity for spherical and non-spherical metal objects. Detectability of metal objects of any kind is very good across the whole detection zone DZ.

FIG. 4a shows the coil system 6, 6A of FIG. 2 in a view perpendicular to the xz-plane with coil sections 211, 311 and 212, 321 overlapping one another in separate areas A11 and A12. The areas A11 and A12 define cross-sections of two corresponding first imaginary cuboids with volumes v11, v12, which extend between the coil sections 211, 311 and 212, 321.

FIG. 4b shows the coil system 6, 6A of FIG. 4a from an elevated angle from which the mentioned coil sections 211, 311 and 212, 321 can be identified.

FIG. 5b shows the coil system 6, 6A of FIG. 2 in a view perpendicular to the yz-plane with the transmitter coil 2 and the receiver coils 31, 32 overlapping in an area A3. Inclined or perpendicular to the area A3 a third imaginary cuboid with a volume v3 and the cross-section A3 of the closed loops is extending.

In this view, the transmitter coil 2 and the receiver coils 31, 32 appear as a set of conventional coils as installed in conventional one-dimensional metal detection apparatuses. The turns and half turns of the different coil sections are not visible and do not significantly contribute to the third magnetic field Mx generated by the closed loops of the coil system 6, 6A.

FIG. 5b shows the coil system 6, 6A of FIG. 5a from an elevated angle from which the transmitter coil 2 and receiver coils 31, 32 can be identified.

Figure 6:
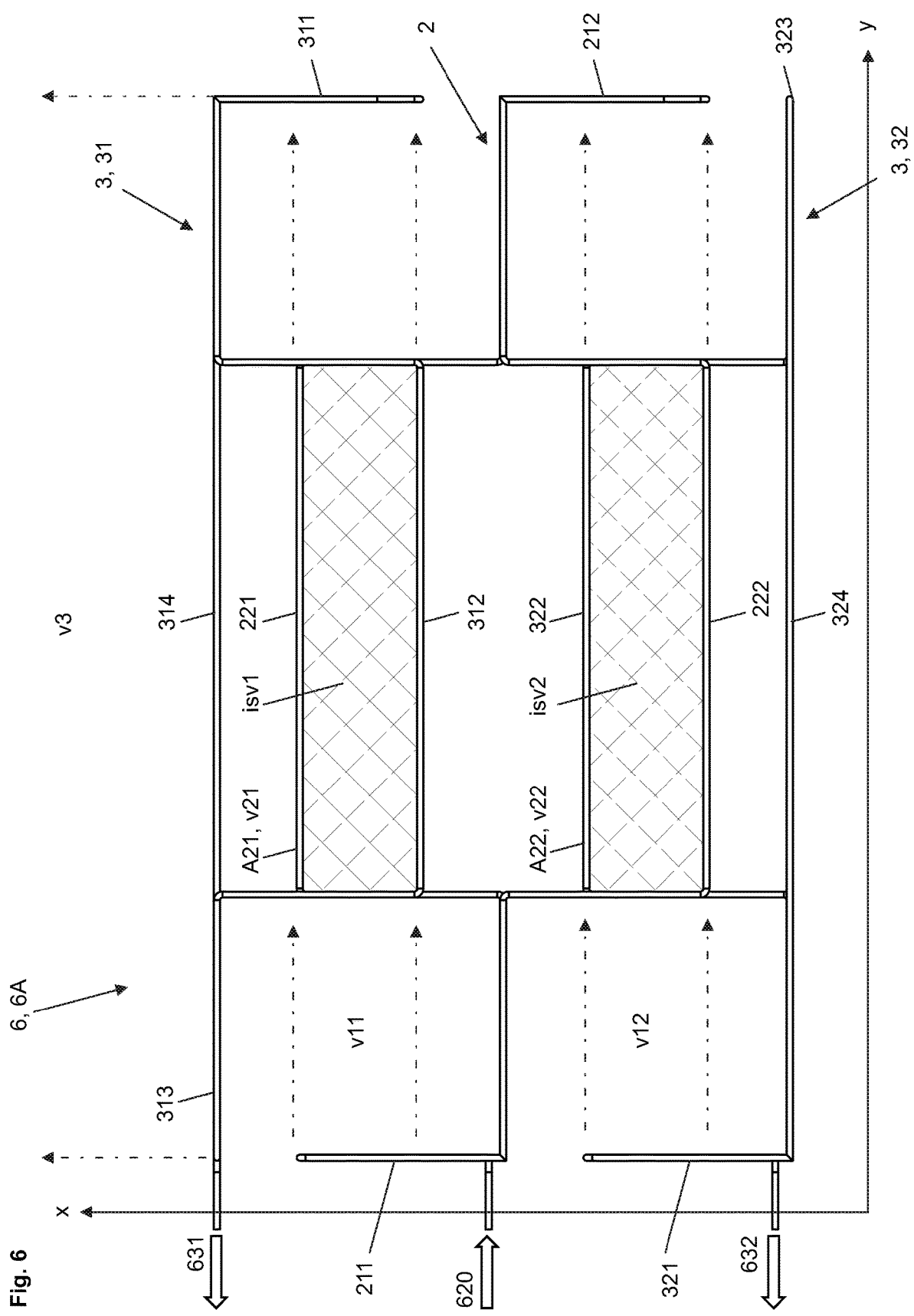
FIG. 6 shows the coil system 6, 6A of FIG. 2 from above in a view perpendicular to the xy-plane with coil sections 221, 312 and 222, 322 overlapping in separate areas A21 and A22.

FIG. 6 shows the coil system 6, 6A of FIG. 2 from above in a view perpendicular to the xy-plane with coil sections 221, 312 and 222, 322 overlapping in separate areas A21 and A22, respectively. Inclined or perpendicular to the areas A21 and A22 further imaginary cuboids with volumes v21, v22 extend along the z-axis.

Figure 9:
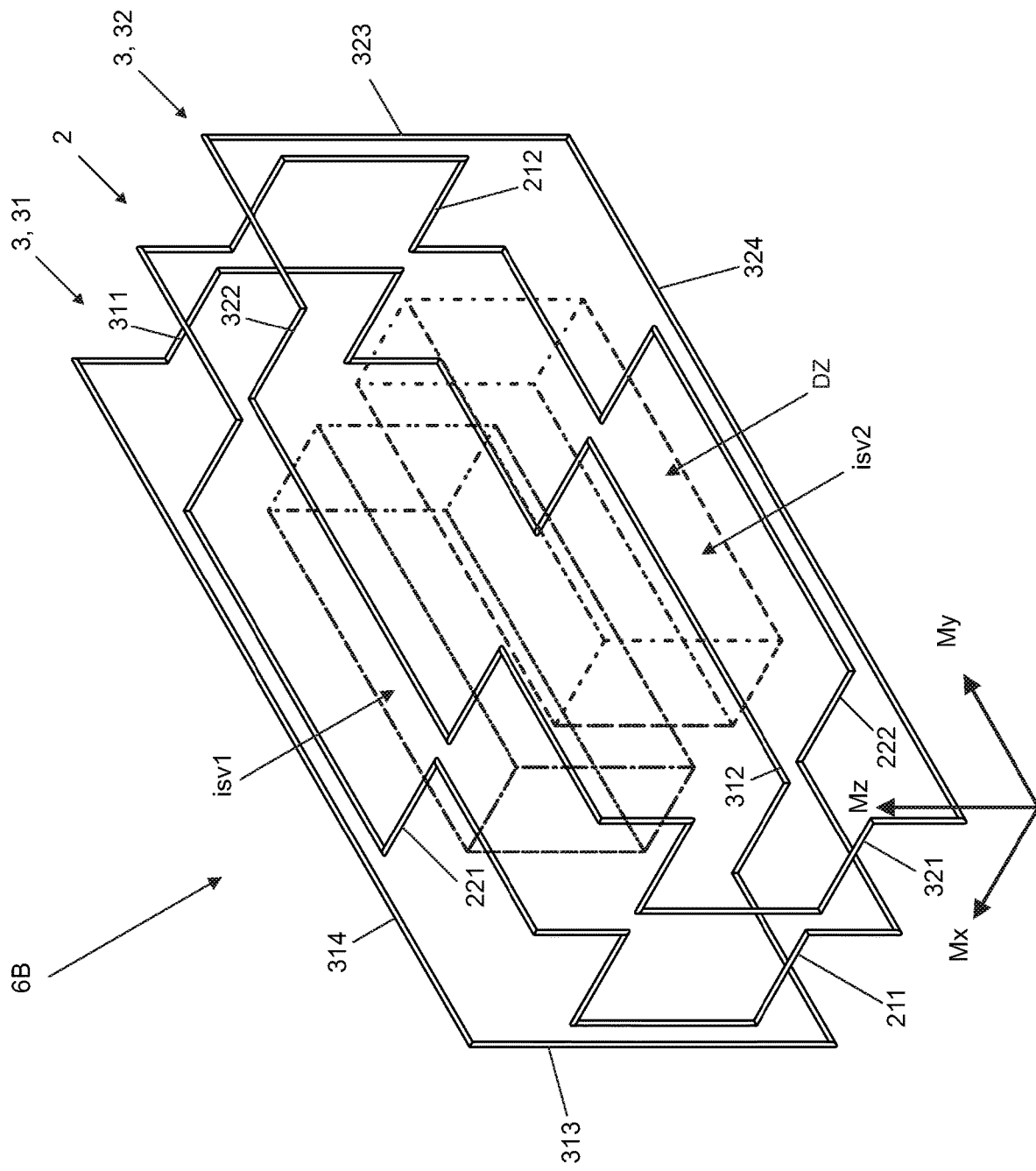
FIG. 9 shows an inventive coil system 6B in a further embodiment with the transmitter coil 2 having four symmetrically shaped rectangular coil sections 211, 212, 221, 222 and the receiver coils 31, 32 each having two symmetrically shaped rectangular coil sections 311, 312 and 321, 322.
Figure 10:
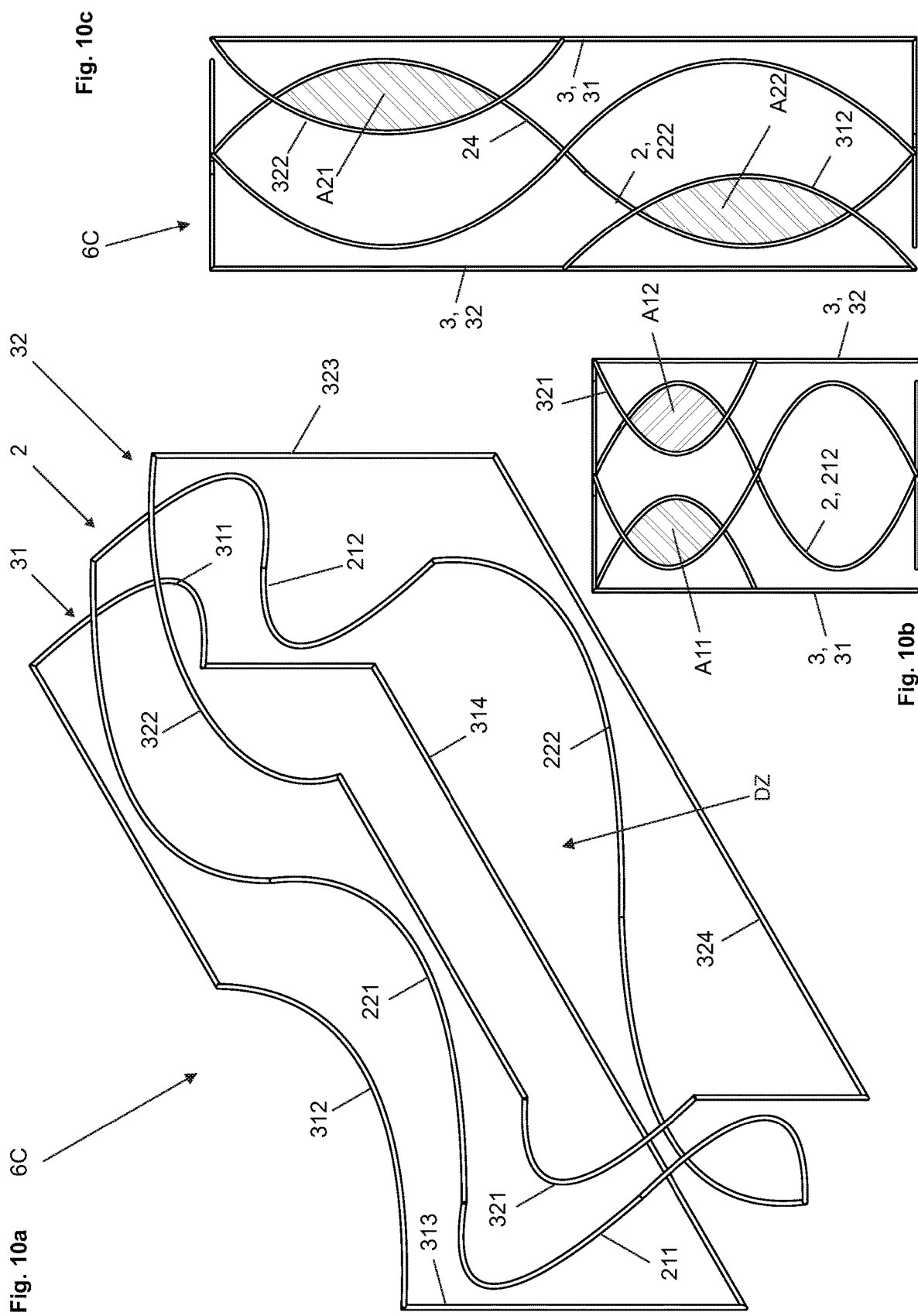
FIG. 10a shows an inventive coil system 6C in a further embodiment with sinusoidal coil sections 211, 212, 221, 222 or elements thereof of the transmitter coil 2 and sinusoidal coil sections 311, 312 and 321, 322 or elements thereof of the receiver coils 31, 32.
FIG. 10b shows the coil system 6c of FIG. 10a from the front side.
FIG. 10c shows the coil system 6c of FIG. 10a from the top.

With dashed arrows the imaginary cuboids with volumes v11, v12 extending along the y-axis and the large hollow imaginary cuboid with volume v3 extending along the z-axis are schematically shown. The intersections of all volumes v11, v12; v21, v22 and v3 define two imaginary cuboids or intersection volumes isv1, isv2 in which typically all three magnetic fields Mx, My, Mz are present and metallic elements of any kind and orientation can be sensed with best results due to the overlapping parts of the receiver coils 31, 32. Such intersection volumes isv1, isv2 are shown in FIG. 9 for a further embodiment 6b of the coil system 6.

Since the coil system 6, 6A forms a cuboid with right angles, the first, second and third magnetic fields My, Mz, Mx are aligned at least approximately orthogonal to one another.

Figure 7:
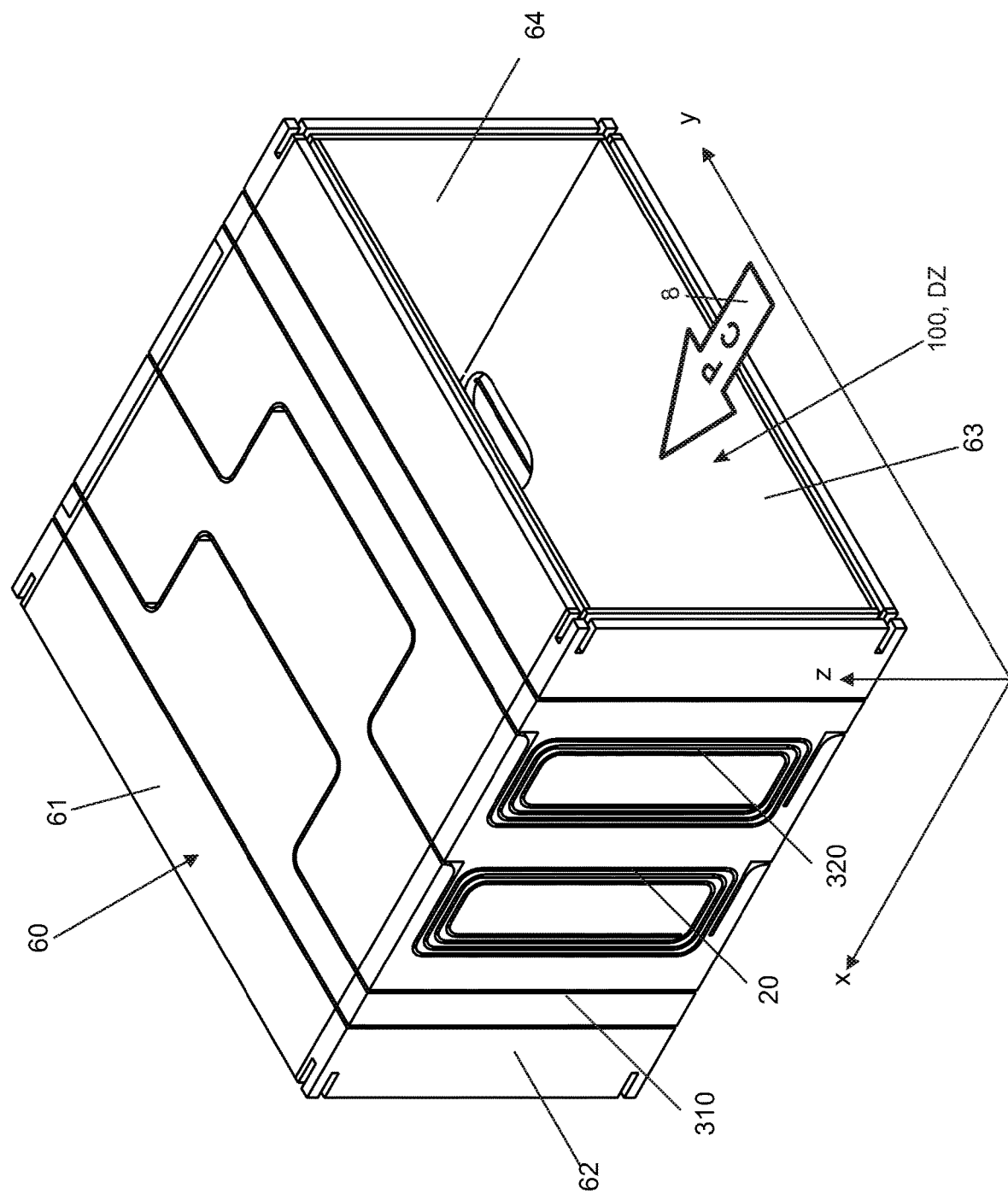
FIG. 7 shows a coil form 60 comprising a transfer passage 100 with a rectangular aspect ratio that consists of four interconnected members 61, 62, 63 and 64, that are provided with grooves 20, 310, 320 into which the transmitter coil 2 and the receiver coils 31, 32 can be placed in one or a plurality of layers.

FIG. 7 shows a non—conducting coil form 60 consisting of four interconnected panels 61, 62, 63 and 64, that are provided with grooves 20, 310, 320 into which the transmitter coil 2 and the receiver coils 31, 32 can be placed in one or a plurality of layers. The four panels 61, 62, 63, 64 are independently manufactured at low cost and can easily be assembled. In the event that a cylindrical or hollow cylindrical detection zone DZ shall be present in the metal detection apparatus, then segments of hollow cylindrical or conical forms can be provided that comprise grooves 20, 310, 320 as well. Of course the coil form 60 can be composed of any number of segments. The coil form 60 or their elements consist of an insulating material, such as plastic. The cross-sections of the grooves 20, 310, 320 are designed such that they can receive a desired number of coil layers.

Figure 8:
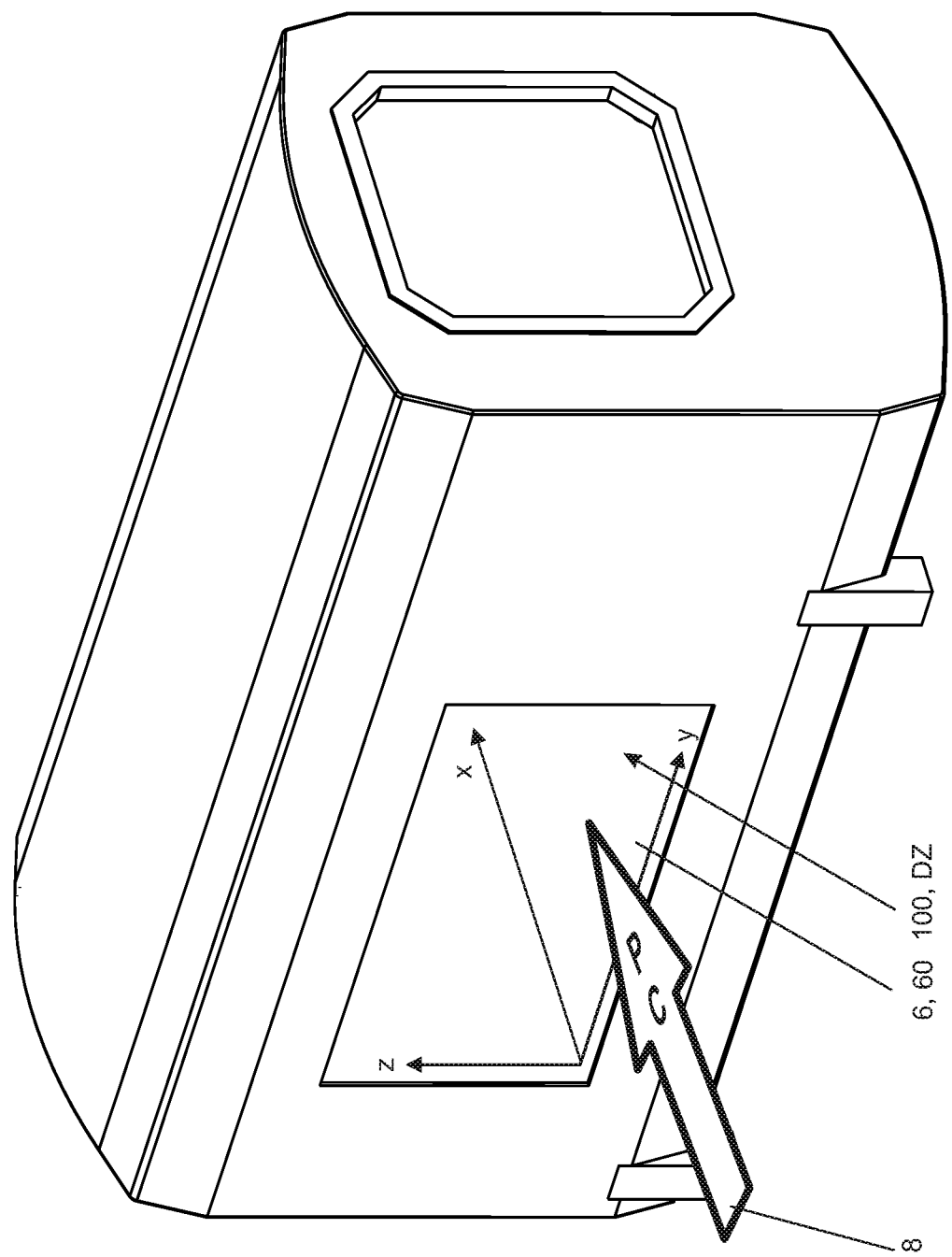
FIG. 8 shows an inventive metal detection apparatus that preferably is equipped with the coil form 60 of FIG. 7 and an inventive coil system 6A for example according to FIG. 2.

FIG. 8 shows an inventive metal detection apparatus that is equipped with an inventive coil system 6 and preferably the coil form 60 of FIG. 7. The coordinate system of the coil system 6 is drawn in the passage channel 100, indicating that the x-axis is extending along the passage channel and that the entrance window has a height extending along the z-axis and a width extending along the y-axis. The aspect ratio of the cross-section of the passage channel 100 or the entrance window is approximately 1:3. An arrow symbolises a conveyor belt 8 on which products P, which may contain contaminants C, are transported through the passage channel 100.

The inventive concept can be implemented with many different embodiments of the coil system 6 defining any geometrical volume with one or a plurality of intersections of the two or three or even more magnetic fields generated by the balanced coil system 6.

FIG. 9 shows an inventive coil system 6B in a further embodiment with the transmitter coil 2 having four symmetrically shaped rectangular coil sections 211, 212, 221, 222 and the receiver coils 31, 32 each having two symmetrically shaped rectangular coil sections 311, 312 and 321, 322 and two remaining straight loop wires 313, 314 and 323, 324 which are aligned perpendicular to one another. The transmitter coil 2 comprises in each plane the same number of turns.

Within the detection zone DZ two separated intersection volumes isv1, isv2 are present, which result from the overlapping of corresponding coil segments. In the intersection volumes isv1, isv2 typically all three magnetic fields Mx, My, Mz intersect and are sensed by corresponding elements of the receiver coils 31, 30. Metal objects, such as wires can be sensed, regardless of their consistency and orientation, with highest sensitivity when travelling through these intersection volumes isv1, isv2.

The coil systems may not only define different intersection volumes isv1, isv2 but may also comprise coil sections with different forms and shapes. Coil sections which correspond to one another and possibly generate a magnetic field preferably comprise identical forms and shapes. The coil sections 211, 212; 221, 222 of the transmitter coil 2 or a part thereof may have a rectangular, curved, circular or sinusoidal shape. As well, the coil sections 311, 312, 313, 314; 321, 322, 323; 324 of the receiver coils 31, 32 may have a rectangular, curved, circular or sinusoidal shape. Coil sections of the transmitter coil 2 and the receiver coils 31, 32, which correspond to one another, preferably comprise identical forms and shapes.

The coil sections of the transmitter coil 2 and the receiver coils 31, 32 may have a symmetrical or asymmetrical shape with reference to a center point. The coil sections may have an asymmetric shape or may have a point-symmetric shape with reference to a center point. E.g., the corresponding first and second coil sections 211, 212 and/or the third and fourth coil sections 221, 222 of the transmitter coil 2 may have an identical symmetrical or asymmetrical shape and may extend in the same or preferably opposite directions.

The coil system 6B of FIG. 9 has a simple design and provides a high sensitivity for spherical and non-spherical metal objects regardless of their orientation.

FIG. 10a shows an inventive coil system 6C with coil sections 211, 212, 221, 222 of the transmitter coil 2 and coil sections 311, 312 and 321, 322 of the receiver coils 31, 32 or elements thereof that have a sinusoidal shape.

FIG. 10b shows the coil system 6c of FIG. 10a from the front side. FIG. 10c shows the coil system 6c of FIG. 10a from the top. It can be seen that coil sections overlap in areas A11, A12; A21, A22. In the intersection zones resulting from the projection of these areas A11, A12; A21, A22, metal objects can be detected with highest sensitivity.

The coil system 6C avoids corners and can therefore be manufactured with reduced costs and effort. Spherical and non-spherical objects, regardless of their orientation, can be detected with high sensitivity.

Figure 11:
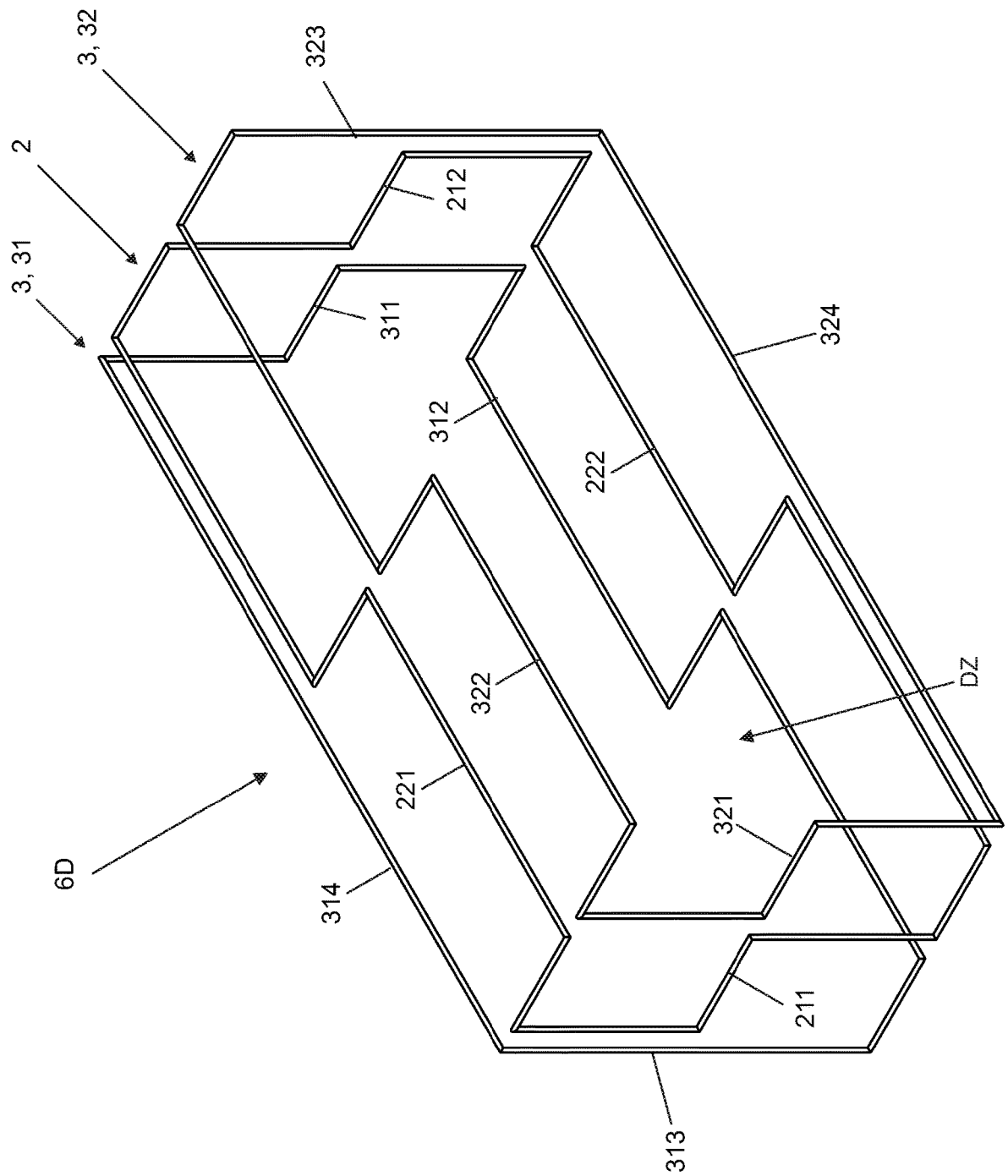
FIG. 11 shows an inventive coil system 6C in a further embodiment with asymmetrical rectangular or stepped coil sections 211, 212, 221, 222 of the transmitter coil 2 and asymmetrical rectangular or stepped coil sections 311, 312 and 321, 322 of the receiver coils 31, 32.

FIG. 11 shows an inventive coil system 6D with asymmetrical rectangular or stepped coil sections 211, 212, 221, 222 of the transmitter coil 2 and asymmetrical rectangular or stepped coil sections 311, 312 and 321, 322 of the receiver coils 31, 32. The coil sections 221, 212; 221, 222 of the transmitter coil 2 and the coil sections 311, 321; 312, 322 of the receiver coils 31, 32 have identical shapes and are oriented in opposite directions.

The first coil sections 311, 321 of the receiver coils 31, 32 have the same shape as the related first or second coil section 211, 212 of the transmitter coil 2 and extend into the opposite direction. The second coil sections 312, 322 of the receiver coils 31, 32 have the same shape as the related third or fourth coil section 221, 222 of the transmitter coil 2 and are extending in the opposite directions.

The coil system 6D of FIG. 11 generates three magnetic fields Mx, My, Mz and allows detection of spherical and non-spherical metal objects, regardless of their orientation with high sensitivity.

FIG. 9, FIG. 10a and FIG. 11 show that the coil sections may follow the shape of an electrical signal, a sinusoidal signal, a saw-tooth signal or a rectangular signal with any duty cycle and phase shift. Corresponding and/or interacting coil sections or preferably provided with identical or inversed shapes.

FIG. 12 shows an inventive coil system 6E with an L-shaped transmitter coil 2 and two L-shaped receiver coils 31, 32.

FIG. 13 shows an inventive coil system 6F with two L-shaped receiver coils 31, 32 and an L-shaped transmitter coil 2 with first and second coil sections 211, 221, that comprise a rectangular subsection 2210, 2210, respectively. Within the intersection of the rectangular subsections 2210, 2210 the medic field is reduced and augmented in the neighbouring zones.

The transmitter coils 2 shown in FIG. 12 and FIG. 13 generate strong magnetic fields My, Mz directed along the y-axis and z-axis and only a week magnetic field along the x-axis. With the strong magnetic fields My, Mz spherical and non-spherical metal objects can be detected with high sensitivity. Due to the lack of a strong third magnetic field Mx non-spherical metal objects may provide a reduced response with specific orientations. The coil systems 6E and 6F have a simple design and can be manufactured with reduced effort and costs.

What is claimed is:

1. An apparatus for detecting metal contaminants in a product travelling in a passage channel of the apparatus, comprising:
a transmitter unit;
a transmitter coil that receives transmitter signals from the transmitter unit;
a first and a second receiver coil, each of which is inductively coupled to the transmitter coil, the respective receiver coils being balanced; and
a receiver unit, arranged to receive, as an input, an output from the respective receiver coils, the outputs being received either separately or combined;
wherein the transmitter coil comprises at least two transmitter coil sections that are arranged inclined to one another and that generate at least a first and a second magnetic field; and
wherein the first and second receiver coils each comprise at least a first receiver coil section that engages in the first magnetic field and at least a second receiver coil section that engages in the second magnetic field.

2. The apparatus of claim 1, wherein:
the respective transmitter coil sections and the first and the second receiver coil sections form closed loops that are distant from one another in third parallel planes; and
the transmitter coil generates a third magnetic field having a closed loop that is sensed by the closed loops of the first and the second receiver coils.

3. The apparatus of claim 2, wherein:
the at least two transmitter coil sections comprise:
a first and a second transmitter coil section that are arranged distant from each other in first parallel planes and that create the first magnetic field; and
a third and a fourth coil section that are arranged distant from each other in second parallel planes and that create the second magnetic field.

4. The apparatus of claim 3, wherein the first, second and third magnetic fields are aligned at least approximately orthogonal to one another.

5. The apparatus of claim 1, wherein at least one of the following conditions is met:
the balanced first and second receiver coils are arranged point-symmetrically or axis-symmetrically relative to one another; and
the transmitter coil is designed point-symmetrically or axis-symmetrically and is located in the center between the first and second receiver coils.

6. The apparatus of claim 2, wherein:
the first receiver coil sections are arranged distant from one another within or in parallel to the first planes; and
wherein the second receiver coil sections are arranged distant from one another within or in parallel to the second planes.

7. The apparatus of claim 1, wherein:
a detection zone is delimited by either the transmitter coil sections or by the transmitter coil sections and the receiver coil sections, such that the detection zone corresponds at least approximately to the passage channel and has a hollow profile that is cylindrical, conical profile or rectangular profile preferably with an aspect ratio in the range from 1:1 to 1:10.

8. The apparatus of claim 7, wherein at least one of the following conditions applies:
the first and second transmitter coil sections on the one hand and the third and fourth transmitter coil sections on the other hand comprise a number of turns with a ratio that corresponds to the aspect ratio of the passage channel; and
the first receiver coil sections on the one hand and the second receiver coil sections on the other hand comprise a number of turns with a ratio that corresponds to the aspect ratio of the passage channel.

9. The apparatus of claim 3, wherein:
the first and second transmitter coil sections and the first receiver coil sections, which are arranged distant from one another in the first parallel planes, overlap one another in a projection perpendicular to the first planes, thus defining at least a first area of overlap;
the third and fourth transmitter coil sections and the second receiver coil sections, which are arranged distant from one another in the second parallel planes, overlap one another in a projection perpendicular to the second planes, thus defining at least a second area of overlap; and
the closed loops formed by the transmitter coil, the first receiver coil and the second receiver coil, which are arranged distant from one another in the third parallel planes, overlap one another in a projection perpendicular to the third planes thus defining at least a third area of overlap.

10. The apparatus of claim 9, wherein the areas of overlap form cross sections of primary volumes that extend perpendicular or inclined to the related area of overlap and form at least one intersection defining a secondary volume in which metal objects can be detected with highest sensitivity.

11. The apparatus of claim 1, wherein at least one of the following conditions applies:
   at least one of the transmitter coil sections or a part thereof has a rectangular, curved, circular or sinusoidal shape; and
   at least one of the receiver coil sections has a rectangular, curved, circular or sinusoidal shape.

12. The apparatus of claim 1, wherein:
   the corresponding first and second transmitter coil sections and/or the third and fourth transmitter coil sections have an identical symmetrical or asymmetrical shape and are extending in the same or opposite directions.

13. The apparatus of claim 12, wherein:
   the first receiver coil sections have the same shape as the related first or second transmitter coil section and extend into the same or opposite direction and/or wherein the second receiver coil sections have the same shape as the related third or fourth transmitter coil and are extending in the same or opposite directions.

14. The apparatus of claim 1, wherein the transmitter coil and the receiver coils exhibit a rectangular shape or an L-shape.

15. The apparatus of claim 1, further comprising:
   a non-conductive coil form comprising grooves onto which the transmitter coil and the receiver coils are wound, the coil form preferably consisting of four panels having grooves for receiving the coils, the panels being independently manufactured and assembled.

* * * * *

UNITED STATES PATENT AND TRADEMARK OFFICE
CERTIFICATE OF CORRECTION

PATENT NO. : 10,605,946 B2
APPLICATION NO. : 15/590516
DATED : March 31, 2020
INVENTOR(S) : Zhao It is certified that error appears in the above-identified patent and that said Letters Patent is hereby corrected as shown below:

In the Specification

In Column 8, Line 25, please delete "inventive coil system 6C" and insert -- inventive coil system 6D --.

In Column 9, Line 17, please add -- 55. -- after "channel".

Signed and Sealed this
Fifteenth Day of September, 2020

Andrei Iancu
*Director of the United States Patent and Trademark Office*